(12) United States Patent
Gilbert (10) Patent No.: US 8,665,031 B2
(45) Date of Patent: Mar. 4, 2014

(54) SYSTEM AND METHOD FOR IMPROVED START-UP OF SELF-OSCILLATING ELECTRO-MECHANICAL SURGICAL DEVICES

(75) Inventor: James A. Gilbert, Boulder, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/597,823

(22) Filed: Aug. 29, 2012

(65) Prior Publication Data

US 2012/0319791 A1    Dec. 20, 2012

Related U.S. Application Data

(62) Division of application No. 12/750,419, filed on Mar. 30, 2010, now Pat. No. 8,258,886.

(51) Int. Cl.
*H03B 5/30*    (2006.01)
*A61B 17/32*    (2006.01)

(52) U.S. Cl.
USPC ........... 331/154; 331/173; 331/185; 310/318; 606/169

(58) Field of Classification Search
USPC ............... 310/318; 327/143, 164; 331/34, 78, 331/116 FE, 116 M, 116 R, 154, 158, 160, 331/172, 173, 185; 600/437; 606/169; 708/250, 251, 255
See application file for complete search history.

(56) References Cited

U.S. PATENT DOCUMENTS

| | | | |
|---|---|---|---|
| 3,469,211 A | 9/1969 | Shoh et al. | |
| 3,573,652 A * | 4/1971 | Charters | 331/78 |
| 3,986,136 A * | 10/1976 | Hurlburt | 331/78 |
| 4,277,710 A | 7/1981 | Harwood et al. | |
| 4,587,958 A | 5/1986 | Noguchi et al. | |
| 4,704,587 A * | 11/1987 | Ouyang et al. | 331/116 FE |
| 4,827,911 A | 5/1989 | Broadwin et al. | |
| 4,896,122 A | 1/1990 | Tahernia et al. | |
| 4,922,902 A | 5/1990 | Wuchinich et al. | |
| 4,965,532 A | 10/1990 | Sakurai | |
| 4,973,876 A | 11/1990 | Roberts | |
| 5,041,802 A | 8/1991 | Wei et al. | |
| 5,136,199 A | 8/1992 | Kawai | |
| 5,180,363 A | 1/1993 | Idemoto et al. | |
| 5,208,558 A | 5/1993 | Shigehara et al. | |
| 5,216,338 A | 6/1993 | Wilson | |

(Continued)

FOREIGN PATENT DOCUMENTS

AU    200179486    5/2002
CA    2359403    4/2002

(Continued)

*Primary Examiner* — Levi Gannon (57) ABSTRACT

An oscillating circuit for determining a resonant frequency of an electro-mechanical oscillating device and for driving the electro-mechanical oscillating device at the determined resonant frequency includes a driving circuit and a start-up, impetus injection circuit. The driving circuit is configured to receive one or more reference signals and further configured to provide a driving signal related to the reference signals to the electro-mechanical oscillating device. The start-up, impetus injection circuit is operably coupled to the electro-mechanical oscillating device and configured to selectively provide a start-up excitation signal to the electro-mechanical oscillation device. The start-up, impetus injection circuit is activated upon start-up of the oscillating circuit to drive the electro-mechanical oscillation device and the driving circuit determines a resonant frequency by measuring a parameter related to the resonant frequency of the electro-mechanical oscillating device.

18 Claims, 6 Drawing Sheets

(56) References Cited

U.S. PATENT DOCUMENTS

| | | | |
|---|---|---|---|
| 5,391,144 A | 2/1995 | Sakurai et al. |
| 5,421,829 A | 6/1995 | Olichney et al. |
| 5,532,539 A | 7/1996 | Hielscher |
| 5,534,826 A | 7/1996 | Logan |
| 5,637,947 A | 6/1997 | Kising et al. |
| 5,688,235 A | 11/1997 | Sakurai et al. |
| 5,700,952 A | 12/1997 | Andersen |
| 5,816,476 A | 10/1998 | Buice et al. |
| 5,834,982 A | 11/1998 | Watanabe et al. |
| 5,836,897 A | 11/1998 | Sakurai et al. |
| 5,982,246 A | 11/1999 | Hofhine et al. |
| 6,066,135 A | 5/2000 | Honda |
| 6,163,100 A | 12/2000 | Morizaki et al. |
| 6,183,426 B1 | 2/2001 | Akisada et al. |
| 6,191,662 B1 | 2/2001 | Volk |
| 6,320,298 B1 | 11/2001 | Kawabe |
| 6,480,796 B2 | 11/2002 | Wiener |
| 6,569,109 B2 | 5/2003 | Sakurai et al. |
| 6,570,294 B1 | 5/2003 | Lino et al. |
| 6,588,277 B2 | 7/2003 | Giordano et al. |
| 6,626,926 B2 | 9/2003 | Friedman et al. |
| 6,678,621 B2 | 1/2004 | Wiener et al. |
| 6,679,899 B2 | 1/2004 | Wiener et al. |
| 6,761,690 B2 | 7/2004 | Sakurai et al. |
| 6,819,195 B1 | 11/2004 | Blanchard et al. |
| 6,898,536 B2 | 5/2005 | Wiener et al. |
| 6,984,919 B2 | 1/2006 | Iino et al. |
| 7,092,265 B2 | 8/2006 | Kernahan |
| 7,123,113 B1 | 10/2006 | Brennan et al. |
| 7,179,271 B2 | 2/2007 | Friedman et al. |
| 7,270,646 B2 | 9/2007 | Sakurai et al. |
| 7,273,483 B2 | 9/2007 | Wiener et al. |
| 7,292,114 B2 | 11/2007 | Greenberg |
| 7,332,979 B2 | 2/2008 | Connell et al. |
| 7,475,801 B2 | 1/2009 | Johansen et al. |
| 7,482,888 B1 | 1/2009 | Kleveland |
| 7,513,160 B2 | 4/2009 | Lynch et al. |
| 7,514,844 B2 | 4/2009 | Unkrich |
| 7,528,670 B2 | 5/2009 | Soh |
| 7,579,750 B2 * | 8/2009 | Kurosawa ............... 310/316.02 |
| 7,614,878 B2 | 11/2009 | Paschke et al. |
| 7,859,353 B2 | 12/2010 | Liu et al. |
| 8,207,651 B2 * | 6/2012 | Gilbert ........................ 310/317 |
| 2005/0027311 A1 | 2/2005 | Wiener et al. |
| 2005/0070800 A1 | 3/2005 | Takahashi |
| 2009/0085433 A1 | 4/2009 | Yoshimura |
| 2009/0118751 A1 | 5/2009 | Wiener et al. |
| 2011/0241786 A1 | 10/2011 | Gilbert |

FOREIGN PATENT DOCUMENTS

| | | |
|---|---|---|
| EP | 1199046 | 4/2002 |
| EP | 1201196 | 3/2006 |
| JP | 2000237204 | 9/2000 |

* cited by examiner

SYSTEM AND METHOD FOR IMPROVED START-UP OF SELF-OSCILLATING ELECTRO-MECHANICAL SURGICAL DEVICES

CROSS-REFERENCE TO RELATED APPLICATIONS

This present application is a divisional application of, and claims priority to, U.S. patent application Ser. No. 12/750,419 entitled "SYSTEM AND METHOD FOR IMPROVED START-UP OF SELF-OSCILLATING ELECTRO-MECHANICAL SURGICAL DEVICES", filed on Mar. 30, 2010, now U.S. Pat. No. 8,258,886, which is incorporated by reference herein.

BACKGROUND

1. Technical Field

The invention relates generally to electronic oscillator circuits, and more specifically, circuits and methods for decreasing the start-up time of an oscillating circuit used to drive an electro-mechanical ultrasonic medical device.

2. Background of Related Art

The benefits associated with the use of ultrasonic energy powered devices, and in particular ultrasonic instruments for surgical use, are well known. For example, the use of an ultrasonic generator in conjunction with a surgical scalpel facilitates faster and easier cutting of organic tissue while accelerating coagulation. Improved cutting results from increased body tissue to scalpel contact caused by the high frequency of vibration of the scalpel blade with respect to body tissue. Improved coagulation results from heat generated by contact between the scalpel blade and the body tissue as the scalpel blade is vibrated at a high frequency.

Conventional ultrasonic instruments include a variety of probes (e.g., cutting blades, shears, hook, ball, etc.) adapted for specific medical procedures. The ultrasonic probe is disposed at a distal end, the end furthest away from the surgeon, of the ultrasonic instrument. These ultrasonic instruments are primarily used in a variety of medical procedures including open surgical procedures, luminal procedures and endoscopic procedures.

Ultrasonic instruments are typically intermittently energized by a clinician to create the desired surgical effect (e.g., cutting, bonding, coagulation, etc.). Ideally, the ultrasonic instrument provides an instantaneous response or zero delay time between the time when the clinician energizes the instrument and the time when the surgical effect is delivered. Unfortunately, unlike electro-surgical instruments such as an RF or microwave powered instrument, an ultrasonic instrument is an electro-mechanical system that requires a start-up period during which the mechanical portion of the end effector begins to resonate at the proper oscillation frequency.

The present disclosure provides alternative methods of initiating the start-up of an oscillation circuit. Alternative methods of providing impetus injection for initiating a start-up are also disclosed that may be employed independent of the oscillation feedback type (e.g., positive or negative feedback oscillators, adaptive or fixed frequency oscillators, or self-oscillating PLL based systems).

SUMMARY

The present disclosure relates to an oscillating circuit that determines a resonant frequency of an electro-mechanical oscillating device and drives the electro-mechanical oscillating device at the determined resonant frequency. The oscillating circuit includes a driving circuit and a start-up, impulse injection circuit. The driving circuit is configured to receive one or more reference signals and further configured to provide a driving signal related to the reference signals to the electro-mechanical oscillating device. The start-up, impulse injection circuit is operably coupled to the electro-mechanical oscillating device and configured to selectively provide a start-up excitation signal to the electro-mechanical oscillation device. The start-up, impulse injection circuit is activated upon start-up of the oscillating circuit to drive the electro-mechanical oscillation device and the driving circuit determines a resonant frequency by measuring a parameter related to the resonant frequency of the electro-mechanical oscillating device.

In one embodiment, the driving circuit may determine a resonant frequency of the electro-mechanical oscillating device within one-half cycle of the resonant frequency and in another embodiment the driving circuit may determine a resonant frequency of the electro-mechanical oscillating device within three cycles of the resonant frequency.

The parameter related to the resonant frequency may also be related to the motion of the electro-mechanical oscillating device. The parameters may be selected from a group consisting of current, voltage and mechanical position.

In a further embodiment, the oscillating circuit includes an excitation signal generating circuit and a start-up switch configured to selectively couple the excitation signal generating circuit to the electro-mechanical oscillating device. The excitation signal generating circuit includes a DC voltage source and an energy storage device. The excitation signal generating circuit may be operatively coupled to the DC voltage source in a first condition and operatively coupled to the start-up switch in a second condition. In the first condition, the DC voltage source charges the energy storage device, and, in the second condition, the energy storage device drives the electro-mechanical oscillating device to a position related to a point of maximum amplitude. The energy storage device may include a capacitor.

In another embodiment, the excitation signal generating circuit includes a digital-to-analog signal converter operatively coupled to the start-up switch and configured to generate a time-frequency varying driving signal. The electro-mechanical oscillating device is driven by the time-frequency varying driving signal generated by the digital-to-analog signal converter. The frequency of the time-frequency varying driving signal may vary linearly or exponentially with respect to time.

In another embodiment the excitation signal generating circuit includes a narrowband, pseudo-random noise amplifier circuit configured to generate the excitation signal by a known "pseudo-random" noise sequence signal within a resonant bandwidth or amplifying the noise signal of an external thermal and/or Schottky source band-limited to the resonant bandwidth of the electro-mechanical device. The narrowband, random noise circuit may include a bandpass filter and the bandpass filter may include an analog circuit. The pseudo-random noise sequence may be used by the controller to further identify the characteristics of the electro-mechanical device at resonance using correlative techniques.

A method for starting an electro-mechanical oscillating device having a varying resonant frequency is also disclosed and includes the steps of: generating a start-up excitation signal; applying the start-up excitation signal to an electro-mechanical oscillating device; driving the electro-mechanical oscillating device to a position related to a point of maximum amplitude; removing the excitation signal from the electro-mechanical oscillating device when the electro-mechanical oscillating device is at a position related to the point of maximum amplitude; measuring one or more parameters related to a resonant frequency of the electro-mechanical oscillating device; determining a resonant frequency of the electro-mechanical oscillating device, and driving the electro-mechanical oscillating device at the determined resonant frequency. The parameters may be selected from a current, a voltage and mechanical position.

Another method for starting an electro-mechanical oscillating device having a varying resonant frequency is also disclosed and includes the steps of: generating a time-frequency varying start-up excitation signal; applying the time-frequency varying start-up excitation signal to an electro-mechanical oscillating device; measuring one or more parameters related to a resonant frequency of the electro-mechanical oscillating device while driving the electro-mechanical oscillating device with the time-frequency varying excitation signal; determining the resonant frequency of the electro-mechanical oscillating device; and driving the electro-mechanical oscillating device at the determined resonant frequency. The parameter may be selected from a current, a voltage and mechanical position.

In yet another method for starting an electro-mechanical oscillating device having a varying resonant frequency includes the steps of: generating a noise signal by analog or digital means; amplifying or otherwise limiting a portion of the generated noise signal within a resonant bandwidth; driving the electro-mechanical oscillating device with the start-up excitation signal; measuring one or more parameters related to a resonant frequency of the electro-mechanical oscillating device; determining the resonant frequency of the electro-mechanical oscillating device; and driving the electro-mechanical oscillating device at the determined resonant frequency. The parameters may be selected from a current, a voltage and mechanical position.

DETAILED DESCRIPTION

Embodiments of the present disclosure are described hereinbelow with reference to the accompanying drawings; however, it is to be understood that the disclosed embodiments are merely exemplary of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously-employ the present disclosure in virtually any appropriately detailed structure.

Oscillator Systems

Figure 1A:
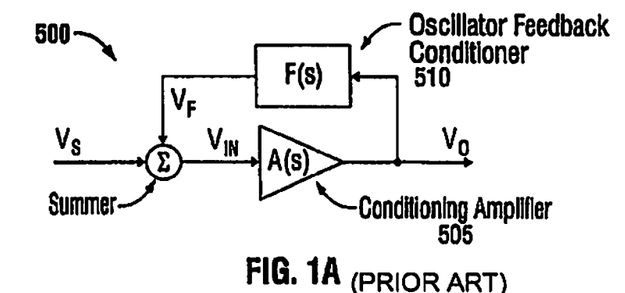
FIG. 1A is a generalized block diagram of a basic oscillator system.

Tuned oscillator systems are described in "Bipolar and MOS analog Integrated Circuit Design, by Alan Grebene (2003) herein incorporated by reference. A tuned oscillator system is normally made up of two basic circuit sections: (1) an amplifier which provides the necessary signal gain; and (2) a feedback network which feeds a part of the amplifier output back to the input. FIG. 1A shows a generalized block diagram 500 of such an oscillator system wherein $V_s$ is the input signal voltage, $V_f$ is the feedback voltage signal generated by feedback network, $V_{in}$ is the sum of $V_s$ and $V_f$ and $V_o$ is equal to $V_{in}$ amplified by the conditioning amplifier 505. For the circuit to oscillate, the conditioning amplifier 505 must provide sufficient gain and the oscillator feedback conditioner 510 must shift the phase of the output signal a sufficient amount such that $V_f$ is in phase with the input signal; $V_{in}$. The total gain around the feedback loop is:

$$V_f/V_{in}=A(j\omega)*F(j\omega)$$

Two Barkhausen Criteria for a circuit to sustain oscillations independent of the input signal voltage are: (a) the signal gain around the loop is a magnitude such that:

$$|V_f/V_{in}|=|A(j\omega)|*|F(j\omega)|\geq 1.0;$$

And, (b) the phase of the signal, φ, around the loop is $$Arg(V_f/V_{in})=\phi_A+\phi_F=0 \text{ or } 360°$$

Figure 1B:
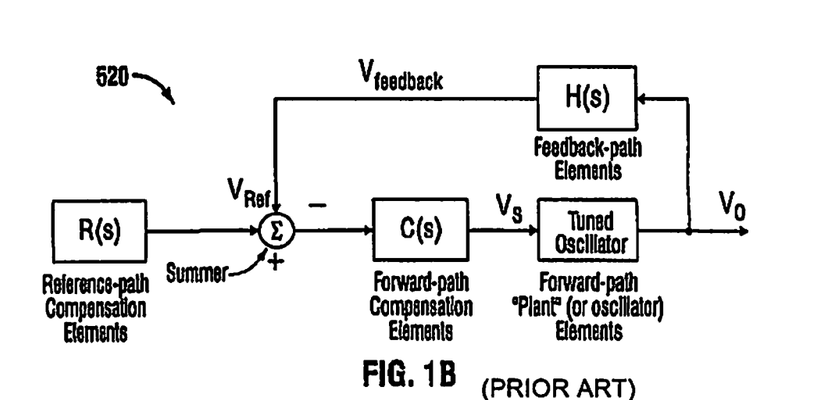
FIG. 1B is a generalized block diagram of the oscillator system in FIG. 1A included within a feedback control loop.

The amplitude at $V_o$ in this simplified representation may be further regulated by including it within a feedback control loop (either by means of a classic PID compensator or a modern Linear Quadratic Regulator (LQR)), as illustrated in FIG. 1B and shown as 520. (See also, *Linear Control System Analysis and Design*, by John D'Azzo et al., (1995), and *Applied Optimal Control and Estimation: Digital Design and Implementation*, by Frank L. Lewis, (1992), both of which are herein incorporated by reference.)

The "tuned oscillators" 525, represented by G(s) in FIG. 1B, may include negative feedback oscillators, positive feedback oscillators, relaxation oscillators, phase-locked loops (PLL) or any other suitable oscillator.

Negative feedback oscillators include a feedback element arranged to introduce about 180° of phase shift at the desired frequency of oscillation, while the amplifier inverts the signal and introduces a sufficient loop gain≥1. This type of oscillator includes, but is not limited to, the common named "Colpitts", "Hartley", Phase-shift", and "Twin-Tee/Notch" oscillators.

Positive feedback oscillators have the feedback elements arranged for minimal phase shift at the desired frequency of oscillation, while the amplifier is non-inverting and introduces sufficient loop gain≥1. This type of oscillator includes, but is not limited to, the common named "Wien-Bridge" and LC-Tuned" oscillators.

Relaxation oscillators (or "multi-vibrators") alternatively charge and discharge a timing capacitor at controlled rates to produce periodic output waveforms. This type of oscillator is typically not used for electro-mechanical medical devices, except as input signal generators for $V_s$.

Figure 1C:
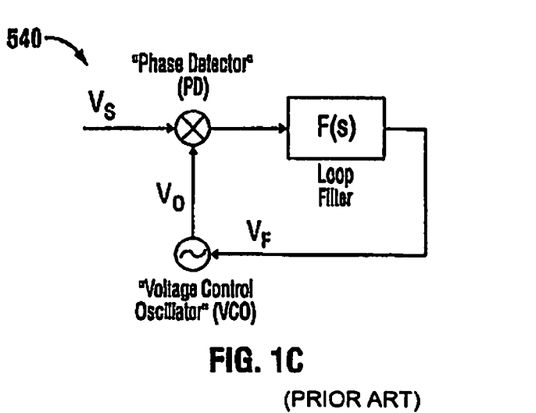
FIG. 1C is generalized block diagram of a basic oscillator system including a Phase-locked loop (PLL)

Phase-locked loops (PLL) are not strictly oscillators, but may be used within a control structure, such as the control system 520 illustrated in FIG. 1B, to operate an electro-mechanical medical device. The block diagram for a PLL 540, as illustrated in FIG. 1C, may be immediately recognized as similar in structure and operation as the oscillator system 500 of FIG. 1A. PLL systems and circuits are taught in Phaselock Techniques, by Floyd Gardner (1979), herein incorporated by reference.

Self-Oscillating Systems

Unlike the "tuned oscillators" described hereinabove, a "self-oscillating" electro-mechanical system (EM system) is one in which the resonance of the electro-mechanical medical device is used within the oscillator feedback loop to provide the band passed oscillation frequency.

The resonant frequency of an electro-mechanical medical device can vary widely depending on temperature and electro-mechanical loading (such as additional mass and/or compliance at the distal end of the system). In addition, each individual electro-mechanical medical device may have its own resonant frequencies that are based on certain parameters such as the materials used, construction and geometry. As such, "driven" or fixed-frequency generators that employ a very narrowband Phase Lock Loop circuit (PLL circuit) or an oscillation circuit that utilizes an oscillating crystal to simply set the resonant frequency are not suitable for dynamically generating the sufficient range of frequencies required for an electro-mechanical medical device.

The electro-mechanical medical device couples to the oscillating circuit to provide energy at the desired resonant frequency to maintain oscillation. The electro-mechanical medical device also couples to the feedback circuitry of the oscillating circuit to provide feedback related to the physical position and/or oscillations of the electro-mechanical medical device. Before the oscillation circuit begins, the electro-mechanical medical device is motionless resulting in no feedback to the oscillating circuit. Therefore, the resonator and accompanying feedback circuit must receive energy from an external source in order for oscillation to commence.

It is generally known that an oscillator start-up requires energy from an external source to overcome mechanical inertia that, to the control loop, exemplifies dead band behavior. The energy from an external source may be applied to a crystal in a nonzero energy state from which the oscillator state evolves. The most efficient stimulus has a frequency equal to the resonant frequency as energy at other frequencies will be rejected by the oscillator. The use of a fixed-frequency oscillator external source for the generation of start-up energy works well for systems with a fixed or known resonant frequency, but this method is ineffective for oscillators with a varying resonant frequency, such as electro-mechanical medical devices.

One solution for this problem is to configure the oscillating circuit so that the circuit is sensitive to thermal and Schottky noise during start-up. Thermal and Schottky noise are low energy white noise and are always present in amplifying circuits. The thermal noise, often referred to as "Johnson noise", due to the thermal agitation of electrons in a conductor is random and uniformly covers all frequencies. The shot noise, often referred to as "Schottky noise" due to random fluctuations in the motion of charge carriers in a conductor, is also random and uniformly covers all frequencies. The oscillation circuit would receive energy across a wide bandwidth as well as at its resonant frequency without the circuit designer having to determine and target the resonant frequency. Oscillation circuits that apply this method involve placing the circuit into two different states. During start-up, the circuit is placed in a first state that amplifies and allows a large amount of noise in the circuit. This high level of noise overcomes the mechanical inertia and decreases the start-up time. After start-up, the circuit transfers into a low noise state for proper operation.

Related support circuits are utilized to determine when oscillation begins so that the primary oscillating circuit can be switched into an operational state at the soonest possible time. These support circuits act to minimize the start-up time, however, power is wasted since white noise has just as much spectral power at the target frequency as it does at other frequencies. The resulting low power of the random wideband noise also limits energy delivery to the oscillating circuit at its resonance, which also increases the required start-up time.

This method for starting self-oscillating electro-mechanical surgical systems is commonly referred to as "kick gain" start-up method. A simple non-surgical system developed by Soh in U.S. patent application Ser. No. 12/098,654 (Soh), and hereby incorporated by reference, utilizes a MOSFET as a gain resistor to increase the loop gain of the common Wein-bridge positive feedback oscillator during the start-up period. While the circuit in Soh delivers some useful energy to the oscillator, much of the energy in the wideband random noise is wasted and the electro-mechanical amplitude is relatively uncontrolled during the start-up period.

Another known method attempts to inject an "impetus" signal into the oscillator through a coupling capacitor—a so-called "Single Frequency Impetus Injection" (SFII) start-up method. U.S. patent application Ser. No. 11/827,947 to Kleveland, and hereby incorporated by reference, discloses an impetus signal injected into the oscillator with a frequency that is an estimate of the resonant frequency of the oscillator and the frequency of the tunable oscillator. The SFII start-up method is well suited for applications where the resonant frequency remains constant or unchanged or the resonant frequency is easily predicted. The SFII start-up method, while effective for electronic systems, is not-well suited for applications where the resonant frequency can vary widely, such as, for example, temperature sensitive systems or electro-mechanical systems under load.

Figure 2:
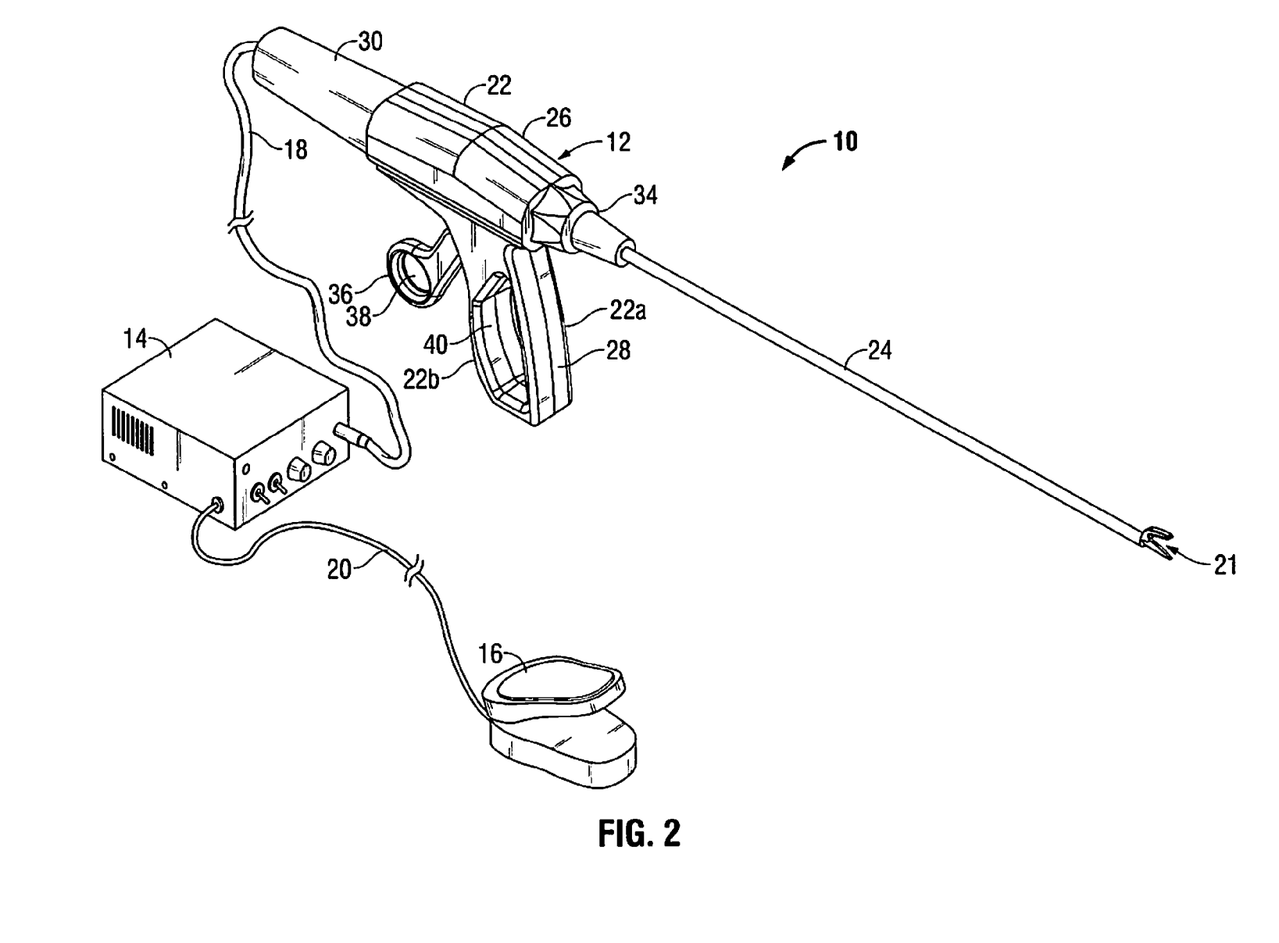
FIG. 2 is a perspective view of an ultrasonic dissection and coagulation system for use with an ultrasonic instrument.

FIG. 2 illustrates an ultrasonic dissection and coagulation system shown generally as system 10. System 10 includes an ultrasonic instrument 12, an ultrasonic generator module 14, and a remote actuator 16. Ultrasonic generator module 14 is operatively connected to ultrasonic instrument 12 by an electrically conductive cable 18 and functions to control the power and frequency of current supplied to ultrasonic instrument 12. Any suitable controller capable of delivering power to ultrasonic instrument 12 can be used. Remote actuator 16, e.g., pedal actuator, is operatively connected to ultrasonic generator module 14 by remote actuator cable 20 and can be actuated to initiate the supply of power to ultrasonic instrument 12 via ultrasonic generator module 14 to effect vibratory motion of ultrasonic instrument 12 to cut and coagulate tissue.

The ultrasonic instrument 12 includes housing 22 and elongated body portion 24 extending distally therefrom. Housing 22 is formed from molded housing half-sections 22a and 22b and includes a barrel portion 26 having a longitudinal axis aligned with the longitudinal axis of elongated body portion 24 and a stationary handle portion 28 extending obliquely from barrel portion 26. Ultrasonic transducer 30 is supported within and extends from the proximal end of housing 22 and is connected to ultrasonic generator module 14 via electrically conductive cable 18. The ultrasonic transducer 30 can be a separate component or incorporated into the ultrasonic instrument 12. The ultrasonic generator module 14 supplies electrical energy having ultrasonic frequency to the ultrasonic transducer 30 to cause oscillation thereof. The ultrasonic transducer 30, which may be one of a variety of electromechanical types, e.g., electrodynamic, piezoelectric, magnetostrictive, is connected to the ultrasonic probe 21 through a vibration coupler (not explicitly shown, contained within barrel portion 26 and elongated body portion 24) and causes ultrasonic oscillation thereof.

The ultrasonic probe 21 is disposed adjacent the distal end of elongated body portion 24 and is actuated by moving the movable handle 36 with respect to stationary handle portion 28. Movable handle 36 and stationary handle portion 28 may include openings 38 and 40, respectively, defined therein that facilitate gripping and actuation of ultrasonic instrument 12. Elongated body portion 24 is supported within rotatable knob 34 and may be selectively rotated by rotatable knob 34 with respect to housing 22 to change the orientation of the distal end of ultrasonic instrument 12.

Those skilled in the art will understand that the ultrasonic probe 21 is an illustrative embodiment of an ultrasonic device and that other types and/or forms of ultrasonic implements are envisioned, such as a blade, a hook, or a ball, and/or an aspirator assembly. An example of an ultrasonic aspirator instrument is shown and described in commonly-owned U.S. Pat. No. 4,922,902 entitled "METHOD FOR REMOVING CELLULAR MATERIAL WITH ENDOSCOPIC ASPIRATOR".

Those skilled in the art will also understand that the ultrasonic dissection and coagulation system 10 and the ultrasonic generator module 14 are provided and explained in detail for example only and should not be construed as limiting the embodiments of the present disclosure. The embodiments disclosed herein may be employed in non-surgical applications including ultrasonic welding, ultrasonic mass flow meters, ultrasonic atomizers or any other suitable electromechanical ultrasonic system that requires the ability to perform intermittent operation.

Figure 3:
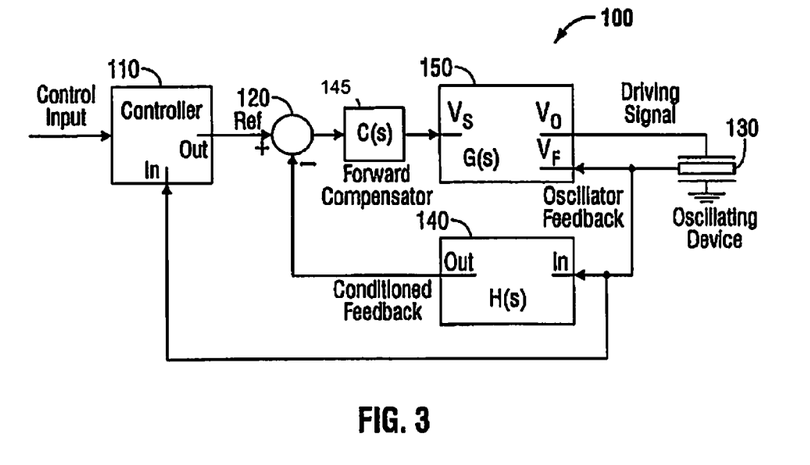
FIG. 3 is a control block diagram of an oscillation circuit for use with the present disclosure.

FIG. 3 is a control block diagram of an oscillation circuit 100 used to drive an oscillating device. Oscillation circuit 100 is disposed within the ultrasonic generator module 14 of FIG. 2 on one or more processors, analog circuits and analog circuit components as is known in the art. Details of the hardware and/or software that implements the various control block embodiments described herein are not provided in detail as implementation of a control system is well known in the art.

Oscillation circuit 100 includes a controller 110, summer 120, a compensator or control process 145, an oscillator conditioner and amplifier 150 and a feedback conditioner 140 that generates and provides a driving signal to the oscillating device 130. The functionality of the individual components 110, 120, 140, 145, 150 of the oscillation circuit 100 are provided to illustrate the embodiments of the present disclosure. The functionality of each functional block may be accomplished by a plurality of devices or components or the functionally of any two or more functional blocks may be consolidated into a single device or component.

Controller 110 provides a reference signal to summer 120 and receives a feedback signal from the oscillating device 130. Controller 110 may be any suitable processor capable of executing logical instructions, performing signal analysis, performing digital signal processing and/or generating a suitable ultrasonic reference signal. Feedback signal received by the controller 110 may be a raw feedback signal from the oscillating device 130, a conditioned feedback signal from the output of the feedback conditioner 140 or both. The controller 110 may also include the elements of forward compensator 145. Oscillating device 130 may include an ultrasonic transducer 30, vibration coupler and/or ultrasonic probe 21 as discussed hereinabove and illustrated in FIG. 2 or any other suitable ultrasonic oscillating device, instrument or arrangement. Feedback is related to the mechanical oscillation of the oscillating device 130 and may be determined by monitoring the physical position of the oscillating device 130, measuring the current and/or voltage of the driving signal and/or generating an electrical signal related to the position of the oscillating device 130 from the movement thereof. Oscillator conditioner and amplifier 150 receives the feedback from the oscillating device 130.

Feedback conditioner 140 is configured to condition the feedback signal from the oscillating device 130. Conditioning of the feedback signal may include filtering and/or amplifying the feedback signal. Feedback conditioner 140 may also be configured to analyze the feedback signal to determine the frequency components thereof. A conditioned feedback signal related to the feedback signal or a generated feedback signal related to one or more parameters of the analysis of the feedback signal is provided to the summer 120. Feedback conditioner 140 and summer 120 may be incorporated into controller 110 in whole or in part and may include analog and/or digital components.

Summer 120 compares the reference signal and the conditioned feedback signal and provides the difference to the forward compensator 145. Forward compensator 145 provides forward path control compensation sufficient for sustaining oscillation at the desired control input settings provided to the controller 110. The oscillator condition and amplifier 150 amplifies the reference signal and provides a driving signal to the oscillating device 130. Controller 110, summer 120, forward compensator 145 and feedback conditioner 140 constitute a feedback control system configured to maintain the oscillating device 130 in a state of oscillation at a resonant frequency provided the oscillator conditioner and amplifier 150 have sufficient operational parameters.

Figure 4:
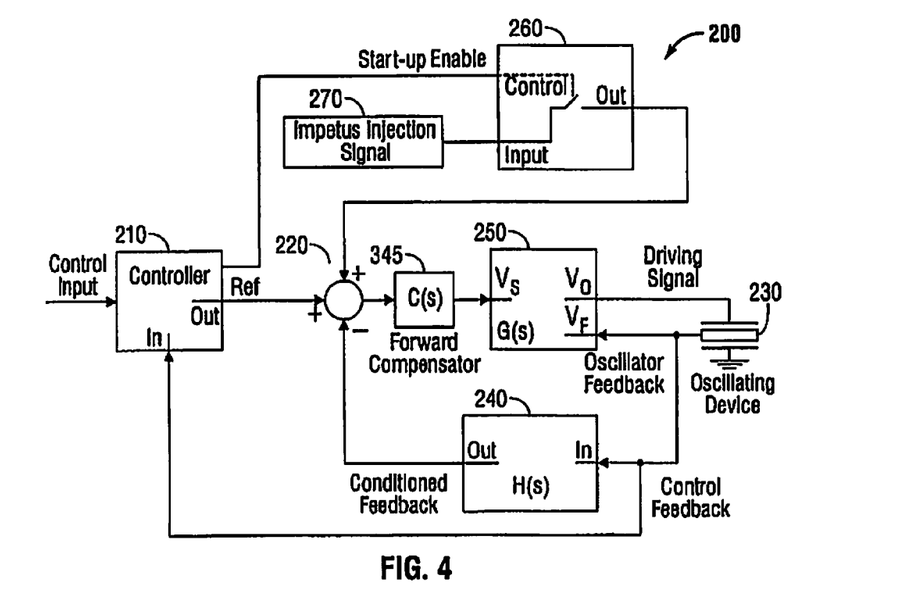
FIG. 4 is the control block diagram of the oscillating circuit of FIG. 3 including a start-up, impulse injection control block according to an embodiment of the present disclosure.

FIG. 4 is the control block diagram of the oscillation circuit 100 of FIG. 3 further including a start-up, impetus injection circuit 270 and a start-up switch 260 according to an embodiment of the present disclosure, the oscillating circuit shown generally as 200. Oscillating circuit 200 includes controller 210, summer 220, forward compensator 345, feedback conditioner 240 and oscillator conditioner and amplifier 250 as described hereinabove and illustrated in FIG. 3 and further includes a start-up switch 260 and start-up, impetus injection circuit 270 operably coupled to the oscillating device 230.

The start-up switch 260 and impetus injection circuit 270 are activated upon start-up of the oscillating circuit 200 to drive the oscillating device 230. For example, the start-up switch 260 may be enabled for a predetermined period of time during the initial start-up of the oscillation circuit 200 such that an excitation signal generated by the start-up, impetus injection circuit 270 is provided to the summer 220. The starting time and the duration of time that the start-up switch 260 is enabled are dependant on the method of start-up, the type of device driven by the oscillation circuit 100 and/or the properties of the excitation signal generated by the start-up, impetus injection circuit 270.

In one embodiment, the start-up switch 260 "enable" signal is provided by the controller 210. Controller 210 may receive one or more user inputs that may be used to enable and/or disable the oscillation circuit 200 or controller 210 may use the one or more inputs as conditions and/or criteria to determine when to enable and/or disable the oscillation circuit 200. For example, an input may be provided from an actuator such as, for example, the remote actuator 16 from FIG. 2. Alternatively, the input may be provided from a clinician. The start-up, impetus injection circuit 270 is activated upon start-up of the oscillation circuit 100 to drive the oscillating device 230 and the oscillation circuit 100 (i.e., the controller) determines a resonant frequency by measuring a parameter related to the resonant frequency of the oscillating device 230.

In another embodiment, controller 210 may selectively implement the start-up, impetus injection circuit 270. For example, controller may determine if start-up of the oscillating circuit 200 requires implementation of the start-up, impetus injection circuit 270 based on the feedback received from the oscillating device.

Figure 5:
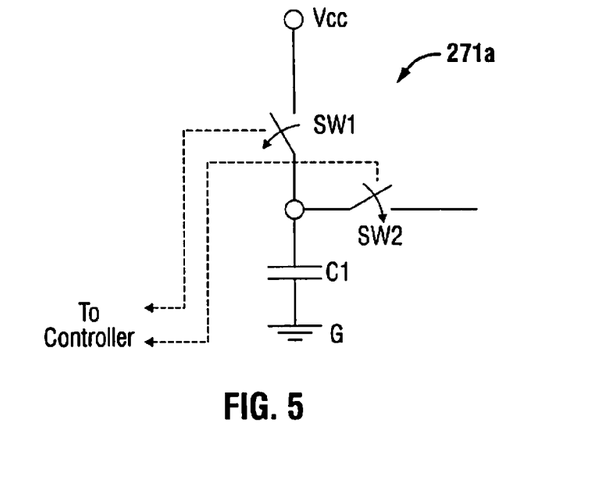
FIG. 5 is a circuit diagram for a capacitive, impulse injection circuit according to another embodiment of the present disclosure.
Figure 6:
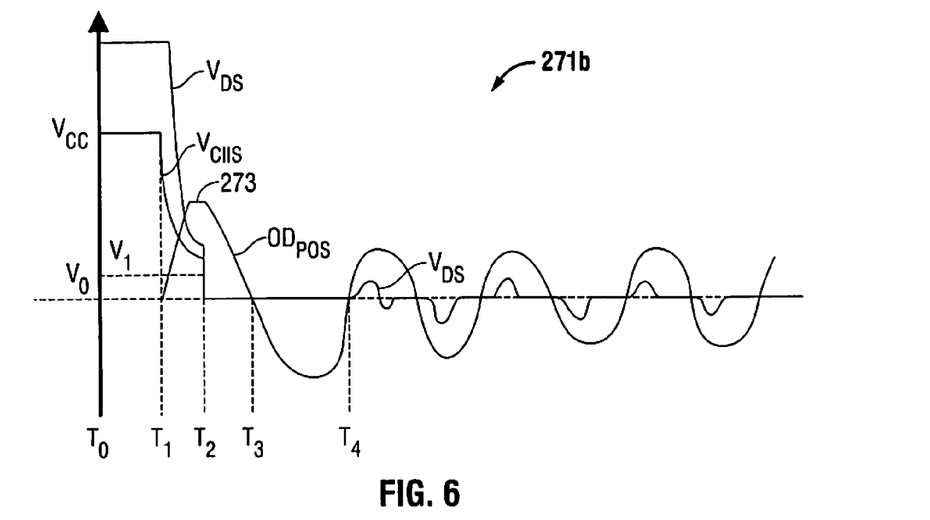
FIG. 6 is a signal diagram of a start-up of an oscillation circuit implementing the capacitive impulse injection circuit of FIG. 4.

Start-up, impetus injection circuit 270 may include an analog circuit that generates an analog signal or may include any suitable algorithm that provides and/or generates an analog or digital signal. Regardless of how the signal is generated (circuit and/or algorithm) or the type of signal generated (analog and/or digital) the signal provided from the start-up, impetus injection circuit 270 is configured to aid in the initialization or start-up of the oscillation circuit 200. Start-up, impetus injection circuit 270 may drive the oscillating device 230 and/or may aid in determining the resonant frequency of the oscillating device 230. FIGS. 5 and 6 describe a circuit diagram 271a and signal diagram 271b, respectively, of a capacitive, impulse-injection circuit according to another embodiment of the present disclosure. System identification by way of impulse response is well known in the art. For example, impulse response is used in hammer impact modal testing. In this implementation of impulse response, unlike previous systems, a capacitor is used to inject an impulse of charge.

FIG. 5 is a circuit diagram of a capacitive impulse injection circuit 271a. The capacitive impulse injection circuit 271a includes a capacitor C1, a first and a second switch SW1, SW2 and a voltage supply $V_{CC}$. In a first state, the first switch SW1 is closed and the second switch SW2 is open. Capacitor C1 connects between the voltage supply $V_{CC}$ and the ground G. The capacitor C1 is pre-charged until the voltage across the capacitor C1 is about equal to the voltage of the voltage supply $V_{CC}$. On start-up, the capacitive impulse injection circuit 271a transitions from a first state to a second state. In the second state the first switch SW1 is open, the second switch SW2 is closed and the capacitor discharges through the second switch SW2 to the capacitive impulse injection input on the start-up switch 260.

In one embodiment, first switch SW1 and second switch SW2 are controlled by the controller 210 of FIG. 4. Controller 210 may selectively utilize the capacitive impulse injection circuit 271a. For example, controller 210 may only utilize the capacitive impulse injection circuit 271a if the resonant frequency of the oscillating device 230 is unknown or a condition occurs that may have changed the resonant frequency of the oscillating device 230. In another embodiment, the capacitive impulse injection circuit 271a is enabled and/or disabled by another controller or other suitable user input or control device.

FIG. 6 is a signal diagram 271b of a start-up circuit implementing the capacitive impulse injection circuit 271a of FIG. 5. At time $T_o$ the capacitive impulse injection signal $V_{CIIS}$ is equal to $V_{CC}$ and the capacitor C1 of the circuit diagram 271a of FIG. 5 is fully charged. At time $T_1$, start-up of the oscillation circuit 200 is enabled, the system transitions from the first state to the second state, as discussed hereinabove, wherein the capacitor C1 discharges through the second switch SW2 and the capacitive impulse injection signal $V_{CIIS}$ is provided to a summer 220. At time $T_1$ the reference from the controller 210 has not been enabled and the feedback from the oscillating device 230 is about equal to zero. As such, the output of the summer 220 is about equal to the capacitive impulse injection signal $V_{CIIS}$ Oscillator conditioner and amplifier 250 amplifies the capacitive impulse injection signal $V_{CIIS}$ from the summer 220 and provides a driving signal $V_{DS}$ to the oscillating device 230 as illustrated in the signal diagram 271b.

Between time $T_1$ and $T_2$, the driving signal $V_{DS}$ drives the oscillating device 230 to a position at (or near) a point of maximum amplitude 273. The oscillating device position is indicated in the signal diagram as $OD_{POS}$. At time $T_2$ the system transitions from the second state to the first state, as discussed hereinabove, and the capacitive impulse injection signal from the start-up switch 260 is disabled. The oscillating device 230, now no longer driven by the driving signal $Y_{DS}$ to the position near maximum amplitude 273, is released. Releasing the oscillating device 230 results in the oscillating device oscillating at one or more resonate frequencies as further illustrated in signal diagram 271b. Oscillator conditioner and amplifier 250 may be pre-configured to sustain oscillation at just a single selected frequency mode of the oscillating device 230 after mechanical inertia has been overcome by the impulse injection.

Most solid objects when struck or released from a position as discussed hereinabove will resonate at one or more resonant frequencies. This reaction is more profound when the object struck or released is specifically designed to resonate. One common example is a tuning fork. A tuning fork is specifically dimensioned and/or designed to oscillate at one specific frequency when struck against a surface, i.e., an impulse. Similarly, the oscillating device 230 is also specifically dimensioned and designed to electro-mechanically resonate at one specific frequency. As such, when released from the driving signal, the oscillating device 230 reacts in a similar manner to the tuning fork by resonating at one or more resonating frequencies. Here, driving the oscillating device 230 with the capacitive impulse injection signal $V_{CIIS}$ is analogous to striking the tuning fork, wherein driving the oscillating device 230 to the point of maximum amplitude 273 provides kinetic energy to the oscillating device 230 and the release from the point of maximum amplitude 273 provides energy to drive the oscillations.

Between time $T_2$ and time $T_4$, the controller 210 measures a parameter related to the resonant frequency of the oscillating device 230 and determines at least one resonant frequency therefrom. For example, the controller 210 may measure a parameter related to the position feedback of the oscillating device 230. The parameter may be a current, a voltage, a parameter related to the mechanical position of the oscillating device 230 and/or calculated velocity or acceleration of the oscillating device 230. Using the parameter, the controller 210 determines at least one resonant frequency of the oscillating device 230.

The measured parameter may be used to determine the equilibrium position (i.e., maximum velocity and acceleration equal to zero), the maximum displacement (i.e., zero velocity and maximum (absolute) acceleration) or any combination thereof. The controller 210 may determine at least one resonant frequency by measuring the time therebetween. For example, a resonant frequency may be determined by measuring the time between two equilibrium positions. As such, the controller may determine a resonant frequency within one half-cycle of the resonant frequency. After determining a resonant frequency, the controller 210 maintains the oscillations of the oscillating device 230 by generating a suitable driving signal.

In another embodiment, a resonant frequency is determined by measuring the period of the oscillations that occur between time $T_1$ and time $T_3$ and the controller 210 may resume control of the oscillations after receiving feedback from as few as one-half cycles of the oscillating device 230. In another embodiment, the controller may determine a plurality of resonant frequencies from measurements made during the first three cycles of the oscillating device 230. A start-up resonant frequency algorithm may utilize the plurality of resonant frequencies and determine a start-up resonant frequency. The algorithm may select the start-up resonant frequency by any calculation or statistical analysis of the plurality of resonant frequencies. For example, the algorithm may include a mean calculation such as, for example, an arithmetic mean, the geometric mean or harmonic mean, a calculation to determine the median frequency and/or any other suitable statistical calculations, such as, for example, a standard deviation calculation to eliminate erroneous frequency values from the plurality of resonant frequencies.

Figure 7:
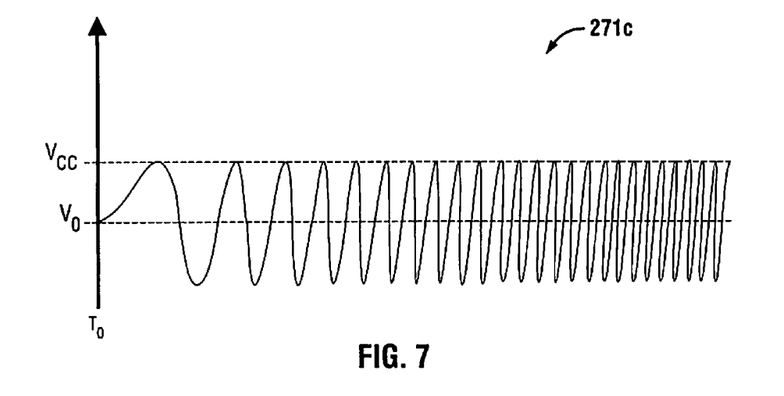
FIG. 7 is a graphical illustration of a chirp, impulse-injection signal according to another embodiment of the present disclosure.

FIG. 7 is a graphical illustration of a chirp, impulse-injection signal 271c that may be utilized by the start-up, impetus injection circuit 270, the start-up switch 260 and the oscillation circuit 200 of FIG. 4. Chirp, impulse-injection signal 271c is applied in a similar manner as a frequency sweep but, instead, the chirp, impulse-injection signal 271c rapidly sweeps frequencies up (or down) at a rate much faster than a full period of any single frequency range. The frequency sweep may be done linearly, as illustrated in FIG. 7. Alternatively, the frequency sweep may be done exponentially over the expected range of resonant frequencies for the specific oscillating device 230. With reference to FIG. 4, a "chirp" signal is generated by the start-up, impetus injection circuit 270. Start-up, impetus injection circuit 270 may include a digital-to-analog signal converter, operatively coupled to the oscillating device 230, configured to generate a time-frequency varying driving signal to drive the oscillating device 230. System identification by way of chirp response is also well known in the art. For example, chirp response is widely used in Time Delay Spectrometry (TDS).

The starting frequency (i.e., the frequency of the first cycle of the chirp signal) and the ending frequency of the chirp, impetus-injection signal 271c (i.e., the frequency of the last cycle of the chirp signal) are selected such that the resonance frequency of the oscillating device 230, or at least the estimated or expected resonance frequency of the oscillating device 230, is represented at or near the midpoint of the chirp, impetus-injection signal 271c.

With reference to FIGS. 4 and 7, the oscillating device 230 is driven with the chirp, impetus-injection signal 271c illustrated in FIG. 7, wherein the resonant frequency of the oscillating device 230 is contained within the frequency range of the chirp, impulse-injection signal 271c. The oscillating device 230 resonates at or about the resonant frequency (contained within the chirp, impetus injection signal 271c) while absorbing all other frequencies. The controller 210 then determines a specific resonant frequency of the oscillating device 230 by monitoring the feedback of the oscillating device 230.

The use of a "chirp" signal is frequently employed in echo-location systems, such as, for example, sonar systems. Chirp signals have also been employed in audio frequency system identification equipment, such as, for example, Time Delay Spectrometry (TDS) devices. In these systems and devices a transducer transmits an ultrasonic frequency varying "chirp" signal and the echo received by a receiving transducer identifies specific objects or locations based on knowledge of the ultrasonic frequencies responses. In other words, the specific signature received from an object is used to identify the object. Unlike sonar systems and TDS devices, the oscillating circuit electro-mechanically drives the oscillating device 230 with the chirp, impulse-injection signal 271c and the controller receives a time varying response from the feedback of the oscillating device 230. Initial oscillation after the chirp has overcome mechanical inertia are sustained by the oscillator conditioner and amplifier 250 pre-configured for a selected resonant frequency mode.

In another embodiment, the frequency of the chirp, impulse-injection signal 271c varies exponentially. One advantage of an exponentially, timed-based chirp, impetus-injection signal is that a broad range of frequencies may be included in the chirp signal as compared with a linearly, time-based chirp, impetus-injection signal. In addition, an exponentially time-based chirp, impetus-injection signal may be better suited to aid in determinating the resonant frequency of ultrasonically oscillating medical devices because the resonant frequency of these devices tend to vary non-linearly with time.

Figure 8:
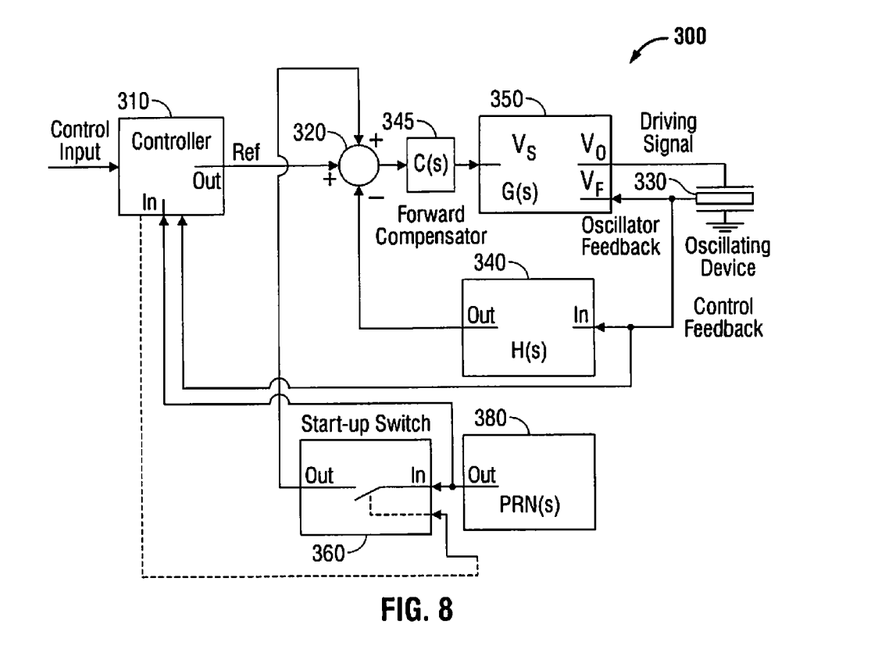
FIG. 8 is a control block diagram of the oscillating circuit of FIG. 3 including a start-up, narrowband, pseudo-random noise injection block according to an embodiment of the present disclosure.

FIG. 8 is a control block diagram of the oscillation circuit 100 of FIG. 3 including a start-up, narrowband, pseudo-random noise generator 380 and a start-up switch 360 according to an embodiment of the present disclosure. The control block is shown generally as 300. Control block 300 includes controller 310, summer 320, forward compensator 345, feedback conditioner 340 and oscillator conditioner and amplifier 350 as described hereinabove and illustrated in FIG. 3 and further includes a pseudo-random noise generator 380 and pseudo-random noise start-up switch 360.

The pseudo-random noise start-up switch 360 is enabled for a predetermined period of time during the start-up of the oscillation circuit 300 and provides a waveform generated by the narrowband pseudo-random noise generator 380 to the summer 320. The use of the pseudo-random noise generator 380, its specific pseudo-random number sequence, and the duration of use may be determined by the controller 310, a user input or any other suitable control system.

In one embodiment, the pseudo-random noise start-up switch 360 "enable" signal is provided by the controller 310. Controller 310 may receive one or more inputs that subsequently enable the oscillation circuit 300. For example, input may be provided from an actuator, such as, for example, the remote actuator 16 from FIG. 2, or input may be a user generated input from a clinician.

Controller 310 may selectively implement the use of the pseudo-random noise generator 380. For example, pseudo-random noise start-up switch 360 enable signal may be an internally generated signal that enables the pseudo-random noise start-up switch 360 if the resonance frequency of the oscillating device 330 is unknown, has changed or if the oscillating device 330 has been replaced, changed or modified. System identification by pseudo-random noise sequences is well known in the art. For example, pseudo-random noise sequences are used for loudspeaker measurements by way of maximum length sequences.

With reference to FIGS. 4 and 8, the controller 210 may receive conditioned feedback from the feedback conditioner 240, as illustrated in FIG. 4, or controller 310 may receive feedback directly from the oscillating device 330. Feedback may be a voltage feedback, a current feedback, feedback related to the real-time mechanical position of the oscillating device 230, 330 or any other suitable feedback that may be used to control an electro-mechanical oscillating device.

Figure 9:
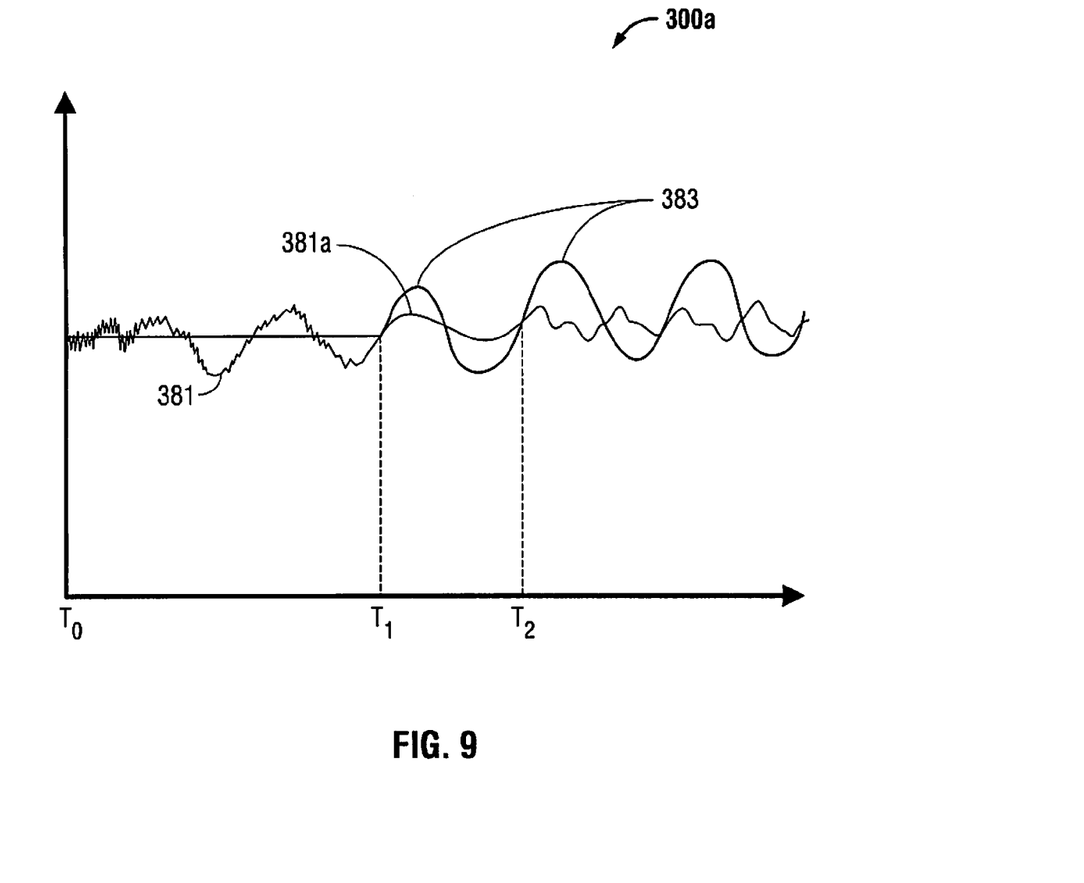
FIG. 9 is a signal diagram of a start-up implementing the start-up, narrowband, pseudo-random noise injection block of FIG. 8.

FIG. 9 is a signal diagram 300a of a start-up circuit implementing the start-up, narrowband, pseudo-random noise generator 380 of FIG. 8. The narrowband, pseudo-random noise signal 381 is injected into the summer 320 of FIG. 8 to drive the oscillating device. At Time $T_0$, the narrowband, pseudo-random noise signal 381 includes a broad range of frequencies (i.e., frequencies typically contained in a noise signal). The pseudo-random noise generator 380 may be selectively designed such that it contains only those frequency bands falling primarily within the resonant bandwidth of the oscillating device 330. Over time, the predominant frequencies within the resonant bandwidth remain and all other frequencies are attenuated or non-existent in the sequence, wherein the predominant frequencies are related to the one or more resonant frequencies of the oscillating device 330. At time $T_1$, the majority of the frequencies outside of the primary resonant bands have been eliminated and the majority of the signal strength of the pseudo-random noise signal 381 is at the resonant frequency of the oscillating device 330.

Between Time $T_0$ and time $T_1$ the pseudo-random noise signal 381 is provided by the narrowband, pseudo random noise generator 380 of the oscillating circuit 300. At time $T_1$ the resonant frequency of the oscillating device 330 is determined by the controller 310, the start-up is complete and the pseudo-random noise start-up switch 360 disables the narrowband, pseudo-random amplifier 380 from injecting the narrowband, pseudo-random noise signal 381 into the summer 320.

With continued reference to FIGS. 8 and 9, at time $T_1$ the driving signal 381a may no longer be provided from the pseudo-random noise start-up switch 360. The controller 310 provides a reference to the summer 320 and the oscillation position 383 of the oscillating device 320 is driven by the narrowband, pseudo-random noise signal 381. Oscillation is sustained by the oscillator conditioner and amplifier 350 pre-configured for a selected resonant frequency mode. Alternatively, the start-up switch 360 could remain closed and system identification and measurement continued for adaptive control by controller 310 of amplitude and/or resonant frequency of oscillating device 330.

A method of starting an oscillating circuit according to an embodiment of the present disclosure is also disclosed and includes the steps of: enabling an impetus injection circuit according to one embodiment of the present disclosure, driving an electro-mechanical oscillating device from a signal provided from the impetus injection circuit, overcoming inertia and determining the resonant frequency of the electro-mechanical oscillating device, disabling the impetus-injection circuit and driving the electro-mechanical oscillating device at the determined resonant frequency.

Another method for starting an electro-mechanical oscillating device, the electro-mechanical oscillating device having a varying resonant frequency, includes the steps of: generating a start-up excitation signal, applying the start-up excitation signal to an electro-mechanical oscillating device, driving the electro-mechanical oscillating device to a position related to a point of maximum amplitude, removing the excitation signal from the electro-mechanical oscillating device when the electro-mechanical oscillating device is at a position related to the point of maximum amplitude, measuring at least one parameter related to a resonant frequency of the electro-mechanical oscillating device, determining a resonant frequency of the electro-mechanical oscillating device, and driving the electro-mechanical oscillating device at the determined resonant frequency. The at least one parameter may be selected from a current, a voltage and mechanical position.

In another method for starting an electro-mechanical oscillating device, the electro-mechanical oscillating device having a varying resonant frequency, includes the steps of: generating a time-frequency varying start-up excitation signal, applying the time-frequency varying start-up excitation signal to an electro-mechanical oscillating device, measuring at least one parameter related to a resonant frequency of the electro-mechanical oscillating device while driving the electro-mechanical oscillating device with the time-frequency varying excitation signal, determining the resonant frequency of the electro-mechanical oscillating device, and driving the electro-mechanical oscillating device at the determined resonant frequency.

In yet another method for starting an electro-mechanical oscillating device, the electro-mechanical oscillating device having a varying resonant frequency, includes the steps of: generating a start-up excitation signal from a pseudo-random noise signal with a narrow bandwidth at or around the resonant frequency, driving the electro-mechanical oscillating device with the start-up excitation signal, measuring at least one parameter related to a resonant frequency of the electro-mechanical oscillating device, determining the resonant frequency of the electro-mechanical oscillating device, and driving the electro-mechanical oscillating device at the determined resonant frequency.

Modification of the above-described systems and methods for using the same, and variations of aspects of the disclosure that are obvious to those of skill in the art are intended to be within the scope of the claims.

What is claimed is:

1. An oscillating circuit for determining a resonant frequency of an electro-mechanical oscillating device and for driving the electro-mechanical oscillating device at the determined resonant frequency, the oscillating circuit comprising:
    a driving circuit configured to receive at least one reference signal and further configured to provide a driving signal related to the at least one reference signal to the electro-mechanical oscillating device;
    a start up excitation signal generating circuit operably coupled to the electro-mechanical oscillating device, wherein the start up excitation signal generating circuit is configured to selectively provide a start-up excitation signal to the driving circuit, and wherein the start up excitation signal generating circuit is activated upon start-up of the oscillating circuit to drive the electro-mechanical oscillation device, the start-up excitation signal generating circuit including:
       a pseudo-random noise generator configured to generate the start-up excitation signal from a digital excitation sequence predetermined to be within the bandwidth of resonance of the electro-mechanical oscillating device; and
       a start-up switch configured to selectively couple the start-up excitation signal to the driving circuit,
    wherein the driving circuit determines a resonant frequency by measuring a parameter related to the resonant frequency of the electro-mechanical oscillating device.

2. The oscillating circuit of claim 1, wherein the start-up excitation signal is coupled to the driving circuit for a predetermined period of time.

3. The oscillating circuit of claim 2, wherein the predetermined period of time is determined by one of a controller and a user input.

4. The oscillating circuit of claim 1, wherein the start-up excitation signal is coupled to the driving circuit upon start-up when the resonance frequency of the electro-mechanical oscillating device is unknown.

5. The oscillating circuit of claim 1, wherein the start-up switch selectively couples the start-up excitation signal to the driving circuit when the resonance frequency of the electro-mechanical oscillating device has changed.

6. The oscillating circuit of claim 1, wherein the start-up switch selectively couples the start-up excitation signal to the driving circuit when a portion of the electro-mechanical oscillating device has changed.

7. The oscillating circuit of claim 1, wherein the start-up switch selectively couples the start-up excitation signal to the driving circuit when a portion of the electro-mechanical oscillating device is modified.

8. A method for starting an electro-mechanical oscillating device, the electro-mechanical oscillating device having a varying resonate frequency, the method comprising:
   generating a start-up excitation signal from a pseudo-random noise generator with a digital excitation sequence predetermined to be within a bandwidth of resonance of the electro-mechanical oscillating device;
   driving the electro-mechanical oscillating device with the start-up excitation signal;
   measuring at least one parameter related to a resonant frequency of the electro-mechanical oscillating device;
   determining a resonant frequency of the electro-mechanical oscillating device; and
   driving the electro-mechanical oscillating device at the determined resonant frequency.

9. The method of claim 8, wherein the at least one parameter is selected from the group consisting of current, voltage and mechanical position.

10. The method of claim 9, further including:
    selectively coupling the start-up excitation signal to the electro-mechanical oscillator for a predetermined period of time, wherein the predetermined period of time is determined by one of a controller or a user input.

11. The method of claim 8, further including enabling the pseudo-random noise generator when the resonance frequency of the electro-mechanical oscillating device has changed.

12. The method of claim 8, further including enabling the pseudo-random noise generator when a portion of the electro-mechanical oscillating device has changed.

13. The method of claim 8, further including enabling the pseudo-random noise generator when a portion of the electro-mechanical oscillating device is modified.

14. A method for starting an electro-mechanical oscillating device, the electro-mechanical oscillating device having a varying resonant frequency, the method comprising:
    generating a time-frequency varying start-up excitation signal from a pseudo-random noise generator configured to generate a time-frequency varying start-up excitation signal from a digital excitation sequence predetermined to be within the bandwidth of resonance of the electro-mechanical oscillating device by activating a start-up switch coupling the pseudo-random noise generator to the electro-mechanical oscillating device;
    applying the time-frequency varying start-up excitation signal to the electro-mechanical oscillating device;
    driving the electro-mechanical oscillating device;
    measuring at least one parameter related to a resonant frequency of the electro-mechanical oscillating device while driving the electro-mechanical oscillating device with the time-frequency varying start-up excitation signal;
    determining the resonant frequency of the electro-mechanical oscillating device; and
    driving the electro-mechanical oscillating device at the determined resonant frequency.

15. The method of claim 14, wherein the at least one parameter is selected from the group consisting of current, voltage and mechanical position.

16. The oscillating circuit of claim 14, wherein applying the time-frequency varying start-up excitation signal to the electro-mechanical oscillating device is performed upon start-up when a portion of the electro-mechanical oscillating device has changed.

17. The oscillating circuit of claim 14, wherein applying the time-frequency varying start-up excitation signal to the electro-mechanical oscillating device is performed upon start-up when the resonance frequency of the electro-mechanical oscillating device is unknown.

18. The oscillating circuit of claim 14, wherein applying the time-frequency varying start-up excitation signal to the electro-mechanical oscillating device is performed upon start-up when the electro-mechanical oscillating device is modified.

* * * * *